United States Patent
Henry et al.

(10) Patent No.: US 11,324,684 B1
(45) Date of Patent: May 10, 2022

(54) THERMAL CONTROL OF HAIR COLOR-ALTERING COMPOSITIONS

(71) Applicant: L'OREAL, Paris (FR)

(72) Inventors: Derek Henry, Jackson Heights, NY (US); Michael Degeorge, Brick, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/390,945

(22) Filed: Jul. 31, 2021

(51) Int. Cl.
| *A61Q 5/08* | (2006.01) |
| *A61K 8/42* | (2006.01) |
| *A61Q 5/10* | (2006.01) |
| *A61K 8/25* | (2006.01) |
| *A61K 8/36* | (2006.01) |
| *A61K 8/23* | (2006.01) |
| *A61K 8/22* | (2006.01) |

(52) U.S. Cl.
CPC .............. *A61K 8/42* (2013.01); *A61K 8/22* (2013.01); *A61K 8/23* (2013.01); *A61K 8/25* (2013.01); *A61K 8/361* (2013.01); *A61Q 5/08* (2013.01); *A61Q 5/10* (2013.01)

(58) Field of Classification Search
CPC ... A61Q 5/08; A61K 8/22; A61K 8/23; A61K 8/19; A61K 8/46; A61K 2800/31; A61K 8/447; A61K 8/022; A61K 2800/24
USPC .......................................................... 424/62
See application file for complete search history.

(56) References Cited

U.S. PATENT DOCUMENTS

| 8,845,756 | B2 | 9/2014 | Pratt et al. | |
| 9,144,534 | B2 | 9/2015 | Pratt et al. | |
| 2006/0123564 | A1* | 6/2006 | Nishizawa | A61Q 5/08 8/405 |
| 2011/0203605 | A1* | 8/2011 | Allard | A61K 8/23 132/208 |
| 2013/0042883 | A1* | 2/2013 | DeGeorge | A61K 8/23 132/208 |
| 2014/0326270 | A1* | 11/2014 | Degeorge | A45D 7/04 132/208 |
| 2017/0007856 | A1* | 1/2017 | Aubert | A45D 37/00 |
| 2018/0116930 | A1* | 5/2018 | Degeorge | A61K 8/22 |
| 2018/0177704 | A1* | 6/2018 | Degeorge | A61Q 5/08 |

FOREIGN PATENT DOCUMENTS

| EP | 2878293 A1 | 6/2015 |
| JP | 2007-131569 A | 5/2007 |
| JP | 2010-280580 A | 12/2010 |
| JP | 2016-193967 A | 11/2016 |
| KR | 10-2010-0105170 A | 9/2010 |
| WO | 2007/137676 A2 | 12/2007 |
| WO | 2012/089665 A2 | 7/2012 |
| WO | 2013/017862 A2 | 2/2013 |

OTHER PUBLICATIONS

Mintel: V-light Nonvolatile Lightening Powder, Matrix, Record ID 1728446, Feb. 2012.
Mintel: "Vision Color Relief Permanent Hair Dye," Schwarzkopf & Henkel, Record ID 335459, Jan. 2005.
Copending U.S. Appl. No. 17/390,943, entitled: "Thermal Control of Hair Color-Altering Compositions," filed Jul. 31, 2021.
Copending U.S. Appl. No. 17/390,946, entitled: " I hermal Control of Hair Color-Altering Compositions," filed Jul. 31, 2021.

* cited by examiner

*Primary Examiner* — Eisa B Elhilo
(74) *Attorney, Agent, or Firm* — The Marbury Law Group, PLLC

(57) ABSTRACT

The disclosure relates to thermal control of compositions for altering the color of hair, in particular to hair bleaching compositions comprising thermal control agents, hair color-altering compositions comprising the hair bleaching compositions and/or thermal control agents, methods for preparing and using the hair color-altering compositions, and kits comprising the hair bleaching compositions and/or thermal control agents.

21 Claims, No Drawings

THERMAL CONTROL OF HAIR COLOR-ALTERING COMPOSITIONS

TECHNICAL FIELD

The present disclosure relates to thermal control of compositions for altering the color of hair, in particular to hair bleaching compositions comprising thermal control agents, hair color-altering compositions comprising the hair bleaching compositions and/or thermal control agents, methods for preparing and using the hair color-altering compositions, and kits comprising the hair bleaching compositions and/or thermal control agents.

BACKGROUND

Consumers want compositions that enhance the appearance of hair, e.g., by changing the color, style, and/or shape of the hair, and/or by imparting various properties to hair, such as shine and conditioning. Many of the known compositions and processes for enhancing the appearance of the hair involve chemical treatment of the hair. The process of changing the color of hair, for example, can involve depositing an artificial color onto the hair which provides a different shade or color to the hair, and/or lifting the color of the hair (bleaching), such as lightening the color of dark hair to lighter shades. The process of lifting the color of hair, also known as lightening, generally requires the use of compositions that comprise at least one oxidizing agent.

Bleaching or lifting the color of the hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone; thus, the higher the number, the lighter the shade or the greater the degree of lift.

To increase the lift attained when bleaching hair, the quantity of persulfates and silicates in the bleaching composition are typically increased, as is the amount of oxidizing agent in the developer composition. However, this increase leads to an increase in temperature when the bleaching composition is mixed with an aqueous developer, for example to temperatures greater than about 70° C. (i.e. greater than about 160° F.), which can result in conditions that are unsafe. However, the more active the bleaching environment is, the more effective it is at lightening hair, which is desired by consumers.

Therefore, there is a need for hair color-altering compositions that are capable of providing high levels of lift (e.g., up to 9 levels) to hair while still maintaining thermal control. It has now surprisingly been discovered that hair color-altering compositions comprising a combination of thermal control agents are able to maintain a peak temperature of less than about 65° C., while imparting up to 9 levels of lift to hair.

SUMMARY

The present disclosure provides compositions that are useful for preparing hair color-altering compositions capable of providing high levels of lift, while maintaining thermal control. Hair color-altering compositions according to the disclosure are prepared by combining a hair bleaching composition and a developer composition, and optionally a thermal control composition. In various embodiments, the hair color-altering composition achieve a peak temperature of less than about 60° C., such as less than about 50° C., while imparting up to 9 levels of lift to hair.

Hair bleaching compositions according to the disclosure may include at least two thermal control agents comprising sodium stearate and ammonium sulfate, at least one persulfate compound, and at least one silicate compound. In various embodiments, the at least one silicate compound may be chosen from sodium silicate, sodium metasilicate, or mixtures thereof. The sodium stearate can be present in an amount of at least about 1.5%, such as at least about 2% or at least about 2.5% by weight, relative to the total weight of the hair bleaching composition. Ammonium sulfate can be present in an amount ranging from about 1% to about 8%, such as about 2.5% to about 6.5%, by weight, relative to the total weight of the hair bleaching composition. The ratio of sodium stearate to ammonium sulfate can be greater than about 1:1, such as greater than about 1.5:1. The at least one silicate can include sodium metasilicate, present in amount of at least 5% by weight, relative to the total weight of the hair bleaching composition. The at least one persulfate compound can be chosen from potassium persulfate, ammonium persulfate, sodium persulfate, or mixtures thereof, present in an amount of at least about 10%, such as at least about 15%, or at least about 20% by weight, relative to the total weight of the hair bleaching composition. The total amount of the thermal control agents can range from about 2.5% to about 20%, such as about 3% to about 18%, or about 5% to about 15% by weight, relative to the total weight of the hair bleaching composition. The hair bleaching composition may be pulverulent, and may include less than 1% water by weight, relative to the total weight of the pulverulent hair bleaching composition. The hair bleaching composition can include oil in an amount of less than about 5% by weight, relative to the total weight of the hair bleaching composition.

Developer compositions typically include at least one oxidizing agent. The at least one oxidizing agent may comprise hydrogen peroxide, which can be present in an amount ranging from about 7.5% to about 20%, such as about 9% to about 18%, or about 11% to about 15% by weight, relative to the total weight of the aqueous developer composition.

Thermal control compositions according to the disclosure comprise at least one thermal control agent chosen from sodium stearate and ammonium sulfate.

The hair color-altering compositions of the present disclosure may be formed by combining a hair bleaching composition according to the disclosure with an aqueous developer composition, at or near the time of use. The hair bleaching composition and the aqueous developer composition can be mixed at a ratio ranging from about 1:3 to 3:1, such as about 1:1 or about 1:1.5. The hair color-altering compositions of the present disclosure may also be formed by combining a hair bleaching composition other than a hair bleaching composition according to the disclosure (e.g., a commercially available hair bleaching composition) with a developer composition and a thermal control composition.

The disclosure also relates to methods for altering the color of the hair by applying a hair color-altering composition according to the disclosure to the hair.

DETAILED DESCRIPTION

The present disclosure relates to thermal control of compositions for altering the color of hair, in particular to hair bleaching compositions comprising thermal control agents, hair color-altering compositions comprising hair bleaching compositions according to the disclosure and/or thermal control agents, methods for preparing and using the hair color-altering compositions, and kits comprising hair bleaching compositions according to the disclosure and/or thermal control agents.

Hair Bleaching Compositions

Hair bleaching compositions according to the disclosure include at least two thermal control agents, at least one persulfate compound, and at least one silicate compound. In some embodiments, the hair bleaching compositions are anhydrous or essentially anhydrous. For example, the hair bleaching composition compositions can include less than about 3%, less than about 2%, less than about 1%, less than about 0.5%, or less than about 0.1% water by weight, relative to the total weight of the hair bleaching composition.

Thermal Control Agents

The hair bleaching compositions include at least two thermal control agents comprising sodium stearate and ammonium sulfate, which in combination surprisingly provide thermal control to hair color-altering compositions.

The total amount of thermal control agents in the hair bleaching composition can range from about 3% to about 20%, such as 4% to about 15%, about 5% to about 12%, about 5.5% to about 10%, about 6% to about 9%, or about 6.5% to about 7.5% by weight, based on the total weight of the hair bleaching composition. In certain embodiments, the total amount of thermal control agents in the hair bleaching composition ranges from about 2% to about 10%, about 3% to about 10%, about 4% to about 10%, about 5% to about 10%, about 6% to about 10%, about 2% to about 9%, about 3% to about 9%, about 4% to about 9%, about 5% to about 9%, about 6% to about 9%, about 2% to about 8%, about 3% to about 8%, about 4% to about 8%, about 5% to about 8%, about 6% to about 8%, about 2% to about 7%, about 3% to about 7%, about 4% to about 7%, about 5% to about 7%, or about 6% to about 7% by weight, based on the total weight of the hair bleaching composition.

The sodium stearate can be present in an amount of at least about 1.5%, at least about 2.5%, such as amounts ranging from about 2% to about 10%, about 2.5% to about 8%, about 3% to about 7%, or about 4% to about 6.5% by weight, relative to the total weight of the hair bleaching composition. In certain embodiments, the amount of sodium stearate ranges from about 2% to about 10%, about 3% to about 10%, about 4% to about 10%, about 2% to about 9%, about 3% to about 9%, about 4% to about 9%, about 2% to about 8%, about 3% to about 8%, about 4% to about 8%, about 2% to about 7%, about 3% to about 7%, about 4% to about 7%, about 2% to about 6%, about 3% to about 6%, about 4% to about 6%, about 2% to about 5%, about 3% to about 5%, or about 4% to about 5% by weight, based on the total weight of the hair bleaching composition.

The ammonium sulfate can be present in an amount of at least about 1.5%, at least about 2%, such as amounts ranging from about 1% to about 10%, such as about 1% to about 9%, about 1.5% to about 8%, about 1.5% to about 7%, or about 2% to about 6% by weight, relative to the total weight of the hair bleaching composition. In certain embodiments, the amount of ammonium sulfate ranges from about 1% to about 10%, about 2% to about 10%, about 3% to about 10%, about 4% to about 10%, about 1% to about 9%, about 2% to about 9%, about 3% to about 9%, about 4% to about 9%, about 1% to about 8%, about 2% to about 8%, about 3% to about 8%, about 4% to about 8%, about 1% to about 7%, about 2% to about 7%, about 3% to about 7%, about 4% to about 7%, about 1% to about 6%, about 2% to about 6%, about 3% to about 6%, about 4% to about 6%, about 1% to about 5%, about 2% to about 5%, about 3% to about 5%, about 4% to about 5%, about 1% to about 4%, about 2% to about 4%, about 3% to about 4%, about 1% to about 3%, or about 2% to about 3% by weight, based on the total weight of the hair bleaching composition.

In various embodiments, the weight ratio of sodium stearate to ammonium sulfate in hair bleaching compositions according to the disclosure may be greater than about 1:1, such as greater than about 1.1:1, greater than about 1.2:1, greater than about 1.3:1, greater than about 1.4:1, greater than about 1.5:1, or greater than about 1.6:1. For example, the weight ratio of sodium stearate to ammonium sulfate may range from about 1:1 to about 2:1, from about 1:1 to about 1.9:1, from about 1:1 to about 1.8:1, or from about 1:1 to about 1.7:1. In certain embodiments, the weight ratio of sodium stearate to ammonium sulfate may be about 1.5:1, about 1.6:1, or about 1.7:1.

In a particular embodiment, the thermal control agent comprises sodium stearate in an amount ranging from about 2% to about 10%, about 2% to about 8%, about 2% to about 6%, or about 3% to about 5%, ammonium sulfate in an amount ranging from about 1% to about 5%, about 1% to about 4%, about 1% to about 3.5%, or about 1.5% to about 3.5%, all weights relative to the total weight of the hair bleaching composition, where the weight ratio of sodium stearate to ammonium sulfate in the hair bleaching composition ranges from about 1:1 to about 1.7:1, about 1.3:1 to about 1.7:1, or about 1.5:1 to about 1.7:1.

Persulfate Compounds

The hair bleaching compositions include at least one persulfate compound. Suitable persulfate compounds can include, but are not limited to, potassium persulfate, ammonium persulfate, sodium persulfate, or mixtures thereof. Persulfate compounds can be present in an amount of at least about 10%, such as at least about 20%, at least about 30%, at least about 40%, or at least about 50% by weight, relative to the total weight of the hair bleaching composition. In some embodiments, the total amount of persulfate compounds can range from about 20% to about 70%, such as about 30% to about 65%, about 45% to about 65%, about 40% to about 60%, about 50% to about 60%, or about 50% to about 55% by weight, relative to the total weight of the hair bleaching composition.

In some embodiments, the weight ratio of the total amount of persulfates to the total amount of thermal control agents in the hair bleaching compositions may be less than about 10:1, less than about 9.8:1, or less than about 9.5:1. In certain embodiments, the weight ratio of the total amount of persulfates to the total amount of thermal control agents in the hair bleaching compositions may range from about 6:1 to about 10:1, such as about 6.4:1 to about 9.6:1.

In various exemplary embodiments, the hair bleaching compositions comprise a mixture of potassium persulfate and ammonium persulfate, present in a total amount ranging from about 45% to about 65% or about 50% to about 60% by weight, relative to the total weight of the hair bleaching composition, wherein the weight ratio of the potassium persulfate and ammonium persulfate to the total amount of thermal control agents in the hair bleaching compositions ranges from about 6:1 to about 10:1 or about 6.4:1 to about 9.6:1, and wherein the weight ratio of sodium stearate to ammonium sulfate is greater than about 1.5:1, for example from about 1:1 to about 2:1.

Silicate Compounds

The hair bleaching compositions also include at least one silicate compound. Non-limiting examples of silicates include lithium, sodium, and potassium silicates, metasilicates, and/or disilicates, and combinations thereof, including mixed lithium, sodium, and potassium salts thereof. Specific non-limiting examples include aluminum silicate, magnesium silicate, aluminum magnesium silicate, calcium silicate, barium silicate, strontium silicate, potassium silicate, potassium metasilicate, sodium silicate, sodium metasilicate, or any mixture thereof. In one embodiment, the at least one silicate compound is chosen from sodium silicate, sodium metasilicate, or mixtures thereof.

The total amount of silicates in the hair bleaching composition may vary, but is typically about 1% to about 40% by weight, based on the total weight of the hair bleaching composition. In some embodiments, the total amount of the one or more silicates is about 1% to about 35%, about 1% to about 30%, about 1% to about 25%, about 1% to about 20%, about 5% to about 40%, about 5% to about 35%, about 5% to about 30%, about 5% to about 25%, about 5% to about 20%, about 10% to about 40%, about 10% to about 35%, about 10% to about 30%, about 10% to about 25%, about 10% to about 20%, about 15% to about 40%, about 15% to about 35%, about 15% to about 30%, about 15% to about 25%, or about 15% to about 20% by weight, based on the total weight of the hair bleaching composition. In some embodiments, the total amount of silicates ranges from about 12% to about 20% or about 14% to about 18% by weight, based on the total weight of the hair bleaching composition.

In some embodiments, the at least one silicate comprises sodium silicate, wherein the sodium silicate is present in an amount of at least about 3%, such as at least about 5% by weight, for example from about 3% to about 10%, about 4% to about 8%, or about 5% to about 7% by weight, based on the total weight of the hair bleaching composition.

In other embodiments, the at least one silicate comprises sodium metasilicate, wherein the sodium metasilicate is present in an amount up to about 20%, such as up to about 18%, or up to about 16%, for example from about 5% to about 20%, about 7% to about 18%, about 10% to about 15%, or about 12% to about 14% by weight, based on the total weight of the hair bleaching composition.

In further embodiments, the weight ratio of the total amount of silicates to the total amount of thermal control agents in the hair bleaching compositions may be less than about 3.5:1, or less than about 3:1. In certain embodiments, the weight ratio of the total amount of silicates to the total amount of thermal control agents in the hair bleaching compositions may range from about 2:1 to about 4:1, such as about 2.2:1 to about 3.7:1.

In various embodiments when the hair bleaching compositions comprises sodium metasilicate, the weight ratio of the sodium metasilicate to the total amount of thermal control agents may range from about 1:1 to about 3:1, such as about 1.5:1 to about 2.6:1.

In further embodiments, the total amount of persulfate compounds and total amount of silicate compounds may be chosen such that the weight ratio of persulfates to silicates ranges from about 1.5:1 to about 3.5:1, for example about 2:1 to about 3:1 or about 2.25:1 to about 2.75:1.

In various exemplary embodiments, the hair bleaching compositions comprise sodium silicate and/or sodium metasilicate, present in a total amount ranging from about 10% to about 30%, or about 15% to about 25% by weight, relative to the total weight of the hair bleaching composition, wherein the weight ratio of the sodium silicate and/or sodium metasilicate to the total amount of thermal control agents in the hair bleaching compositions ranges from about 2:1 to about 4:1 or about 2.2:1 to about 3.7:1, and wherein the weight ratio of sodium stearate to ammonium sulfate is greater than about 1.5:1, for example from about 1:1 to about 2:1.

Additional Components

The hair bleaching compositions may optionally include other components typically used in hair bleaching compositions, but the skilled person will take care to ensure that the additional components do not impair, or do not substantially impair, the thermal control of the thermal control agents.

Oxidizing Agents

The hair bleaching compositions may optionally include one or more oxidizing agents in addition to the at least one persulfate compound. For example, the one or more additional oxidizing agents may be selected from the group consisting of perborates, percarbonates, salts thereof, or mixtures thereof. In some embodiments, the hair bleaching compositions can include, as additional oxidizing agents, one or more of alkali metal bromates, ferricyanides, redox enzymes such as laccases, peroxidases, and 2-electron oxidoreductases, such as uricase. These oxidizing agents may be used in place of or in combination with one or more oxidizing agents selected from the group consisting of perborates, percarbonates, a salt thereof, and a mixture thereof.

The total amount of additional oxidizing agents in the hair bleaching compositions may vary but is typically about 5% to about 45%, such as from about 5% to about 40%, from about 5% to about 35%, from about 5% to about 30%, from about 5% to about 25%, from about 5% to about 20%, from about 5% to about 15%, or from about 5% to about 10% by weight, based on the total weight of the hair bleaching composition. In at least one embodiment, the hair bleaching composition is free or substantially free of oxidizing agents other than the persulfates described above.

Alkaline Agents

Optionally, the hair bleaching compositions may include one or more alkaline agents other than the at least one silicate compound. By way of example, alkanolamines, organic amines, basic amino acids, salts thereof, or mixtures thereof may be chosen. Non-limiting examples of alkanolamines include monoethanolamine and triethanolamine. Non-limiting examples of organic amines include 2-amino-2-methyl-1-propanol (AMP), 2-amino-2-methyl-1,3-propanediol, and guanidine. Non-limiting examples of basic amino acids include arginine, glycine, and lysine. In other embodiments, additional alkaline agents may be chosen from inorganic alkaline agents such as sodium hydroxide, potassium hydroxide, calcium hydroxide, magnesium hydroxide, magnesium carbonate hydroxide, barium hydroxide, sodium phosphate, potassium phosphate, ammonium carbonate, sodium carbonate, potassium carbonate, or magnesium carbonate. Mixtures of any of the above additional alkaline agents may be used, for example glycine and magnesium carbonate hydroxide.

The total amount of the one or more additional alkaline agents other than the silicate compounds may vary, but may range from about 0.1% to about 20% by weight, based on the total weight of the hair bleaching composition. In some embodiments, the total amount of the one or more alkaline agents other than the silicate compounds ranges from about 0.1% to about 15%, about 0.1% to about 13%, about 0.1% to about 11%, about 1% to about 15%, about 1% to about 13%, about 1% to about 11%, about 3% to about 15%, about 3% to about 13%, about 3% to about 11%, about 5% to about 15%, about 5% to about 13%, or about 5% to about 11% by weight, based on the total weight of the hair bleaching composition.

Thickening Agents

The hair bleaching composition may optionally include one or more thickening agents. Non-limiting examples of thickening agents include carboxylic acid/carboxylate copolymers, hydrophobically-modified cross-linked copolymers of carboxylic acid and alkyl carboxylate vinyl polymers, methyl cellulose, ethyl cellulose, hydroxyethyl cellulose, hydroxylpropyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, polyethyleneimine, bentonite, aluminum magnesium silicate, laponite, hectonite, anhydrous silicic acid, or mixtures thereof. In some embodiments, guar gum is particularly useful. In some embodiments, it may be preferable to exclude cellulose thickeners, such as cellulose gum, etc.

The total amount of the one or more thickening agents may vary, but typically ranges from about 0.1% to about 10% by weight, based on the total weight of the hair bleaching composition. In some embodiments, the total amount of thickening agents may range from about 0.1% to about 8%, such as about 0.1% to about 6%, about 0.1% to about 4%, about 0.5% to about 10%, about 0.5% to about 8%, about 0.5% to about 6%, about 0.5% to about 12%, about 0.5% to about 10%, about 0.5% to about 8%, about 0.5% to about 6%, about 0.5% to about 4%, about 1% to about 10%, about 1% to about 8%, about 1% to about 6%, about 1% to about 4%, or about 1% to about 3% by weight, based on the total weight of the hair bleaching composition.

Oils

In some embodiments, the hair bleaching composition includes one or more oils. The oils may include those generally used in cosmetics and particularly oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or organ fluorinated oils, volatile or non-volatile silicone oils, fluorosilicone oils and their mixtures. Mention is made, as an example of linear or branched hydrocarbons, of oils of mineral or synthetic origin, such as liquid paraffins and their derivatives, petrolatum, mineral oils, polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

If present, the total amount of the one or more oils in the hair bleaching composition may vary but is typically less than about 5%, such as about 0.1% to about 5% by weight, based on the total weight of the hair bleaching composition. In some embodiments, the total amount of the one or more oils may be about 0.1% to about 4%, about 0.1% to about 3%, about 0.1% to about 2%, or about 0.1% to about 1% by weight, based on the total weight of the hair bleaching composition.

In a preferred embodiment, the hair bleaching composition comprises mineral oil, which is present in an amount less than 5%, less than 4%, or less than 3% by weight, relative to the total weight of the hair bleaching composition.

Acids

Optionally, the hair bleaching composition may comprise one or more acid. The acids are typically non-polymeric and may have one (mono), two (di), or three (tri) carboxylic acid groups (—COOH). The non-polymeric mono, di, and tricarboxylic acids, and/or salts thereof, typically have a molecular weight of less than about 500 g/mol, less than about 400 g/mol, or less than about 300 g/mol.

Non-limiting examples of monocarboxylic acids include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof.

Non-limiting examples of dicarboxylic acids include oxalic acid, malonic acid, malic acid, glutaric acid, citraconic acid, succinic acid, adipic acid, tartaric acid, fumaric acid, sebacic acid, azelaic acid, dodecanedioic acid, phthalic acid, isophthalic acid, terephthalic acid, 2,6-naphthalene dicarboxylic acid, a salt thereof, and a mixture thereof.

Non-limiting examples of tricarboxylic acids include citric acid, isocitric acid, aconitric acid, propane-1,2,3-tricarboxylic acid, benzene-1,3,5-tricarboxylic acid, a salt thereof, and a mixture thereof.

The total amount of the one or more acids may vary but is typically about 0.01% to about 5%, based on the total weight of the hair bleaching composition. In some cases, the total amount of the one or more acids is about 0.01% to about 4%, about 0.01% to about 3.5%, about 0.1% to about 5%, about 0.1% to about 4%, about 0.1% to about 3.5%, about 1% to about 5%, about 1% to about 4%, or about 1% to about 3.5% by weight, based on the total weight of the hair bleaching composition.

Auxiliary Components

Auxiliary components may also optionally be included in the hair bleaching compositions such as, for example, preservatives, cationic conditioning compounds including cationic conditioning polymers, rheology-modifying agents, chelating agents, fatty substances, fragrances, colorants, fillers, amino acids, surfactants (cationic, anionic, nonionic, and/or amphoteric), dessicants, de-dusting agents, ceramides, pH adjusting agents, etc. Such auxiliary components may be present in an amount ranging from about 0.001% to about 5%, such as about 0.01% to about 3%, or about 0.1% to about 2%.

The hair bleaching compositions of the present disclosure may be provided in a variety of different forms. For example, the bleach composition may be a solid, a powder (pulverulent), a gel, a paste, etc. In a preferred embodiment, the hair bleaching composition is pulverulent, and comprises less than 1%, less than 0.5%, or less than 0.1% water.

Thermal Control Compositions

Optionally, the thermal control agents may be present in a composition other than the hair bleaching composition.

In some embodiments, the thermal control compositions include at least two thermal control agents comprising sodium stearate and ammonium sulfate. In various embodiments, the weight ratio of sodium stearate to ammonium sulfate in the thermal control compositions may be greater than about 1:1, such as greater than about 1.1:1, greater than about 1.2:1, greater than about 1.3:1, greater than about 1.4:1, greater than about 1.5:1, or greater than about 1.6:1. For example, the weight ratio of sodium stearate to ammonium sulfate may range from about 1:1 to about 2:1, from about 1:1 to about 1.9:1, from about 1:1 to about 1.8:1, or from about 1:1 to about 1.7:1. In certain embodiments, the weight ratio of sodium stearate to ammonium sulfate may be about 1.5:1, about 1.6:1, or about 1.7:1.

In further embodiments, a thermal control composition may comprise a first thermal control agent chosen from sodium stearate and ammonium sulfate, which may be mixed with a hair bleaching composition, developer composition, and/or another composition, e.g. a second thermal control composition, comprising a second thermal control agent chosen from sodium stearate and ammonium sulfate, so that the ratio of sodium stearate and ammonium sulfate in the mixture is greater than about 1:1, such as greater than about 1.1:1, greater than about 1.2:1, greater than about 1.3:1, greater than about 1.4:1, greater than about 1.5:1, or greater than about 1.6:1, for example range from about 1:1 to about 2:1, from about 1:1 to about 1.9:1, from about 1:1 to about 1.8:1, or from about 1:1 to about 1.7:1, or are about 1.5:1, about 1.6:1, or about 1.7:1. For example, a first thermal control agent in an exemplary thermal control composition may be chosen from sodium stearate, and the thermal control composition may be mixed with a hair bleaching composition or a second thermal control composition comprising ammonium sulfate, where the mixture comprises sodium stearate and ammonium sulfate in the recited weight ratios.

The thermal control compositions may optionally include additional components, such as fillers or excipients, or other components that may be typical in a hair color-altering composition, such as alkalizing agents and oxidizing agents. Thus, the thermal control compositions may comprise, consist essentially of, or consist of the thermal control agents. For example, the thermal control compositions may comprise, consist essentially of, or consist of sodium stearate, may comprise, consist essentially of, or consist of ammonium sulfate, may comprise, consist essentially of, or consist of sodium stearate and ammonium sulfate, may comprise, consist essentially of, or consist of sodium stearate and/or ammonium sulfate and at least one filler (e.g., talc), etc.

Hair Color-Altering Compositions

The hair color-altering compositions according to the disclosure comprise thermal control agents in order to reduce the peak temperature of the composition. The hair color-altering compositions may, in some embodiments, be formed by mixing a hair bleaching composition according to the disclosure with a developer composition. In further embodiments, the hair color-altering compositions are formed by mixing a hair bleaching composition not according to the disclosure, e.g., a commercially available hair bleaching composition, with a developer composition and a thermal control composition. In addition, the hair color-altering compositions may include any additional components typically used in hair color-altering compositions, but the skilled person will take care to ensure that the additional components do not impair, or do not substantially impair, the thermal control of the thermal control agents.

Thermal Control Agents

Hair color-altering compositions according to the disclosure comprise at least two thermal control agents comprising sodium stearate and ammonium sulfate. The total amount of thermal control agents comprising sodium stearate and ammonium sulfate in the hair color-altering composition can range from about 1.2% to about 10%, such as 1.6% to about 7.5%, about 2% to about 6%, about 2.2% to about 5%, about 2.4% to about 4.5%, or about 2.6% to about 3.75% by weight, based on the total weight of the hair color-altering composition. In certain embodiments, the total amount of thermal control agents in the hair color-altering composition ranges from about 0.8% to about 5%, about 1.2% to about 5%, about 1.6% to about 5%, about 2% to about 5%, about 1.2% to about 5%, about 0.8% to about 4.5%, about 1.2% to about 4.5%, about 1.6% to about 4.5%, about 2% to about 4.5%, about 2.4% to about 4.5%, about 0.8% to about 4%, about 1.2% to about 4%, about 1.6% to about 4%, about 2% to about 4%, about 2.4% to about 4%, about 0.8% to about 3.5%, about 1.2% to about 3.5%, about 1.6% to about 3.5%, about 2% to about 3.5%, about 2.1% to about 3.2%, or about 2.4% to about 3.5% by weight, based on the total weight of the hair color-altering composition.

The sodium stearate can be present in an amount of at least about 0.6%, such as amounts ranging from about 0.8% to about 5%, about 1% to about 4%, about 1.2% to about 3.5%, or about 1.6% to about 2.6% by weight, relative to the total weight of the hair color-altering composition. In certain embodiments, the amount of sodium stearate ranges from about 0.8% to about 5%, about 1.2% to about 5%, about 1.6% to about 5%, about 0.8% to about 4.5%, about 1.2% to about 4.5%, about 1.6% to about 4.5%, about 0.8% to about 4%, about 1.2% to about 4%, about 1.6% to about 4%, about 0.8% to about 3.5%, about 1.2% to about 3.5%, about 1.6% to about 3.5%, about 0.8% to about 3%, about 1.2% to about 3%, about 1.6% to about 3%, about 0.8% to about 2.5%, about 1.2% to about 2.5%, or about 1.6% to about 2.5% by weight, based on the total weight of the hair color-altering composition.

The ammonium sulfate can be present in an amount ranging from about 0.4% to about 5%, such as about 0.4% to about 4.5%, about 0.6% to about 4%, about 0.6% to about 3.5%, or about 1.2% to about 3% by weight, relative to the total weight of the hair color-altering composition. In certain embodiments, the amount of ammonium sulfate ranges from about 0.4% to about 5%, about 0.8% to about 5%, about 1.2% to about 5%, about 1.6% to about 5%, about 0.4% to about 4.5%, about 0.8% to about 4.5%, about 1.2% to about 4.5%, about 1.6% to about 4.5%, about 0.4% to about 4%, about 0.8% to about 4%, about 1.2% to about 4%, about 1.6% to about 4%, about 0.4% to about 3.5%, about 0.8% to about 3.5%, about 1.2% to about 3.5%, about 1.6% to about 3.5%, about 0.4% to about 3%, about 0.8% to about 3%, about 1.2% to about 3%, about 1.6% to about 3%, about 0.4% to about 2.5%, about 0.8% to about 2.5%, about 1.2% to about 2.5%, about 1.6% to about 2.5%, about 0.4% to about 2%, about 0.8% to about 2%, about 1.2% to about 2%, about 0.4% to about 1.5%, or about 0.8% to about 1.5% by weight, based on the total weight of the hair color-altering composition.

In various embodiments, the weight ratio of sodium stearate to ammonium sulfate in the hair color-altering compositions may be greater than about 1:1, such as greater than about 1.1:1, greater than about 1.2:1, greater than about 1.3:1, greater than about 1.4:1, greater than about 1.5:1, or greater than about 1.6:1. For example, the weight ratio of sodium stearate to ammonium sulfate may range from about 1:1 to about 2:1, from about 1:1 to about 1.9:1, from about 1:1 to about 1.8:1, or from about 1:1 to about 1.7:1. In certain embodiments, the weight ratio of sodium stearate to ammonium sulfate may be about 1.5:1, about 1.6:1, or about 1.7:1.

Developer Compositions

The developer compositions comprise at least one oxidizing agent, and a cosmetically suitable carrier, for example water. In some embodiments, the developer composition is aqueous and the oxidizing agent comprises, consists essentially of, or consists of hydrogen peroxide. The total amount of oxidizing agent and water in the developer composition can vary depending on the desired strength of the developer composition.

Cosmetic Carrier

The developer compositions comprise a cosmetically suitable carrier, which may, in certain embodiments, include water. The total amount of water may vary, but in some embodiments ranges from about 40% to about 96% by weight, based on the total weight of the developer composition. In some embodiments, the total amount of water ranges from about 50% to about 96%, about 60% to about 96%, about 70% to about 96%, about 80% to about 96%, about 83% to about 95%, about 60% to about 95%, about 70% to about 95%, or about 80% to about 95% by weight, based on the total weight of the developer composition.

Optionally, the developer composition may comprise one or more additional solvents in addition to water in the carrier. For example, organic solvents may be included in the developer compositions. By way of example only, organic solvent may be chosen from monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. If present, the additional solvent may be in the developer composition in a total amount ranging up to about 10%, such as about 0.01% to about 10%, about 0.01% to about 5%, about 0.1% to about 5%, about 0.1% to about 4%, about 0.1% to about 3%, about 0.1% to about 2%, or about 0.1% to about 1% by weight, based on the total weight of the developer composition.

Oxidizing Agents

The developer composition comprises at least one oxidizing agent. As useful oxidizing agents, hydrogen peroxide, urea peroxide, alkali metal bromates, alkali metal ferricyanides, and persalts, such as perborates or persulphates, may be chosen. Use may also be made of one or more oxidation-reduction enzymes, such as laccases, peroxidases and 2-electron oxidoreductases (such as uricase), optionally in the presence of their respective donor or cofactor.

In various embodiments, the total amount of oxidizing agent in the developer composition ranges from about 1% to about 30% by weight, based on the total weight of the developer composition. For instance, the total amount of oxidizing agent may be about 1% to about 20%, about 1% to about 15%, about 1% to about 12%, about 3% to about 20%, about 3% to about 15%, about 3% to about 12%, about 5% to about 20%, about 5% to about 15%, about 5% to about 12%, about 7% to about 20%, about 7% to about 15%, about 7% to about 12%, about 9% to about 20%, about 9% to about 15%, or about 9% to about 12% by weight, based on the total weight of the developer composition. The total amount of oxidizing agent is preferably at least about 7%, at least about 8%, at least about 9%, at least about 10%, at least about 11%, or at least about 11.5%, such as at 8% to about 12%, about 9% to about 12%, about 10% to about 12%, about 11% to about 12%, or is about 9%, about 10%, about 11%, or about 12% by weight, based on the total weight of the developer composition.

In one embodiment, the developer composition is aqueous and comprises hydrogen peroxide as an oxidizing agent, where the hydrogen peroxide is present in the aqueous developer composition in an amount ranging from about 5% to about 20%, such as about 7% to about 15%, about 8% to about 13%, about 8% to about 10%, about 9% to about 13%, or about 10% to about 12%, for example about 7%, about 8%, about 9% about 10%, about 11% about 12%, about 13%, about 14%, or about 15% by weight, based on the total weight of the developer composition. The aqueous developer composition may thus be, for instance, 20V, 30V, or 40V hydrogen peroxide developers, preferably 30V or 40V, and most preferably 40V.

Non-Ionic Surfactants

The developer compositions may optionally include at least one non-ionic surfactant. Non-limiting classes of non-ionic surfactants include esters of polyols with fatty acids and alkoxylated derivatives thereof, alkylpolyglucosides, sucrose esters, alkoxylated ethers of fatty acids and glucose or alkylglucose, esters of fatty acids and glucose or alkylglucose, sorbitol esters of fatty acids and alkoxylated derivatives thereof, alkoxylated fatty alcohols (for example, ethoxylated fatty alcohols), alkanolamides, or mixtures thereof.

The alkoxy groups for the alkoxylated surfactants may, for example, be chosen from C2-C6 oxides and their mixtures, with ethylene oxide, propylene oxide, and their mixtures being the preferred alkoxides. The alkyl chain may be linear, branched, saturated, or unsaturated.

In one embodiment, the non-ionic surfactant comprises at least one alkoxylated, e.g., ethoxylated, fatty alcohol or derivative thereof. As used herein, "fatty alcohol" refers to any alcohol with a carbon chain of CS or greater, such as, for example, C8 or greater, C10 or greater, and C12 or greater. The at least one fatty alcohol may be chosen from, for example, C9-C11 alcohols, C12-C13 alcohols, C12-C15 alcohols, C12-C16 alcohols, or C14-C15 alcohols, or may be chosen from arachidyl alcohol, behenyl alcohol, caprylic alcohol, cetearyl alcohol, cetyl alcohol, coconut alcohol, decyl alcohol, hydrogenated tallow alcohol, jojoba alcohol, lauryl alcohol, myristyl alcohol, oleyl alcohol, palm alcohol, palm kernel alcohol, stearyl alcohol, tallow alcohol, and tridecyl alcohol. Non-limiting examples of alkoxylated fatty alcohols include Non-limiting examples of the at least one alkoxylated fatty alcohol include ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, laureth-1, laureth-2, laureth-3, laureth-4, laureth-5, laureth-6, laureth-7, laureth-8, laureth-9, laureth-10, laureth-11, laureth-12, laureth-13, laureth-14, laureth-15, laureth-16, laureth-20, laureth-23, laureth-25, laureth-30, laureth-40, deceth-3, deceth-5, oleth-5, oleth-30, steareth-2, steareth-10, steareth-20, steareth-100, cctylsteareth-12, ceteareth-5, ceteareth-5, polyglyceryl 4-lauryl ether, polyglyceryl 4-oleyl ether, polyglyceryl 2-oleyl ether, polyglyceryl 2-cetyl ether, polyglyceryl 6-cetyl ether, polyglyceryl 6-oleylcetyl ether, polyglyceryl 6-octadecyl ether, C9-C11 pareth-3, C9-C11 pareth-6, C11-C15 pareth-3, C11-C15 pareth-5, C11-C15 pareth-12, C11-C15 pareth-20, C12-C15 pareth-9, C12-C15 pareth-12, and C22-C24 pareth-33, or mixtures thereof. Optionally, the at least one fatty alcohol may be chosen as a mixture or compound with the non-alkoxylated fatty alcohol. For example, the non-ionic surfactant may comprise ceteareth-25 and cetearyl alcohol.

Also useful herein as nonionic surfactants are alkyl glycosides, which are the condensation products of long chain alcohols, e.g., C8-C30 alcohols, with sugar or starch polymers. These compounds can be represented by the formula (S)n-O—R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a C8-C20 alkyl group, and n is an integer of from about 1 to about 9. Commercially available examples of these surfactants include decyl polyglucoside and lauryl polyglucoside. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16-C22 saturated, unsaturated and branched chain fatty acids, such as polyglyceryl-4 isostearate, polyglyceryl-oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of C16-C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate, sorbitan sesquioleate, sorbitan monoisostearate, sorbitan stearates, sorbitan trioleate, sorbitan tristearate, sorbitan dipalmitates, and sorbitan isostearate.

If present, the amount of non-ionic surfactant may range from about 0.1% to about 10%, such as about 1% to about 10%, about 1% to about 8%, about 1% to about 6%, or about 2% to about 4% by weight, relative to the total weight of the developer composition. In certain embodiments, the amount of non-ionic surfactant ranges from about 0.1% to about 6%, about 0.1% to about 5%, about 0.1% to about 4%, about 0.1% to about 3%, 0.5% to about 6%, about 0.5% to about 5%, about 0.5% to about 4%, about 0.5% to about 3%, about 1% to about 6%, about 1% to about 5%, about 1% to about 4%, about 1% to about 3%, about 1.5% to about 6%, about 1.5% to about 5%, about 1.5% to about 4%, about 1.5% to about 3%, about 2% to about 6%, about 2% to about 5%, about 2% to about 4%, about 2% to about 3%, or about 2.5% to about 3.5% by weight, based on the total weight of the developer composition.

Additional Components

The developer compositions may optionally include other components typically used in developer compositions, such as, for example, rheology-modifying agents, chelants, fatty substances, ceramides, pH adjusting agents, preservatives, fragrances, surfactants other than non-ionic surfactants, etc.

The developer composition may be in the form of a powder, gel, liquid, foam, lotion, cream, mousse, or emulsion. In some embodiments, the developer is anhydrous, and is mixed with water prior to or simultaneously with being mixed with a hair bleaching composition (and optionally with a thermal control composition) to form the hair color-altering composition. The pH of the developer composition is typically acidic, and may range from about 1 to about 6, such as from about 2 to about 5.

In an exemplary and non-limiting embodiment, a hair color-altering composition comprises (1) a hair bleaching composition including at least two thermal control agents comprising sodium stearate and ammonium sulfate, at least one persulfate compound, and at least one silicate compound, wherein the weight ratio of sodium stearate to ammonium sulfate is greater than about 1:1, such as greater than about 1.1:1, greater than about 1.2:1, greater than about 1.3:1, greater than about 1.4:1, greater than about 1.5:1, or greater than about 1.6:1, for example range from about 1:1 to about 2:1, from about 1:1 to about 1.9:1, from about 1:1 to about 1.8:1, or from about 1:1 to about 1.7:1, or is about 1.5:1, and (2) a developer composition comprising at least one oxidizing agent. In this embodiment, the weights are given relative to the total weight of the composition in which they are present prior to mixing to form the hair color-altering composition.

In a further exemplary and non-limiting embodiment, a hair color-altering composition comprises (1) a hair bleaching composition, (2) a developer composition comprising at least one oxidizing agent, and (3) a thermal control composition, wherein the hair bleaching composition, developer composition, and/or thermal control composition comprise at least one persulfate compound and/or at least one silicate compound, such that the hair color-altering composition comprises at least one persulfate compound and at least one silicate compound, and wherein the hair bleaching composition, developer composition, and/or thermal control composition comprise sodium stearate and/or ammonium sulfate in total combined amounts so that when mixed to form the hair color-altering composition, the ratio of sodium stearate to ammonium sulfate in the mixture is greater than about 1:1, such as greater than about 1.1:1, greater than about 1.2:1, greater than about 1.3:1, greater than about 1.4:1, greater than about 1.5:1, or greater than about 1.6:1, for example range from about 1:1 to about 2:1, from about 1:1 to about 1.9:1, from about 1:1 to about 1.8:1, or from about 1:1 to about 1.7:1, or is about 1.5:1, about 1.6:1, or about 1.7:1.

In a still further exemplary and non-limiting embodiment, a hair color-altering composition comprises at least two thermal control agents comprising sodium stearate and ammonium sulfate, at least one persulfate compound, at least one silicate compound chosen from sodium silicate, sodium metasilicate, or mixtures thereof, at least one oxidizing agent, and water, wherein the ratio of sodium stearate to ammonium sulfate is greater than about 1:1, such as greater than about 1.1:1, greater than about 1.2:1, greater than about 1.3:1, greater than about 1.4:1, greater than about 1.5:1, or greater than about 1.6:1, for example range from about 1:1 to about 2:1, from about 1:1 to about 1.9:1, from about 1:1 to about 1.8:1, or from about 1:1 to about 1.7:1, or is about 1.5:1, about 1.6:1, or about 1.7:1, and wherein the peak temperature of the hair color-altering composition is less than about 60° C.

Methods of Preparing Hair Color-Altering Compositions Having Thermal Control

The hair color-altering compositions of the present disclosure may be aqueous mixtures formed by mixing a hair bleaching composition according to the disclosure and a developer composition at or near the time of use, and/or by mixing a thermal control composition, a hair bleaching composition not according to the disclosure, and a developer composition at or near the time of use. The hair color-altering compositions may be referred to as "ready-to-use" compositions because these compositions are typically ready to be applied to hair in order to alter the color of the hair. Thus, methods of preparing hair color-altering compositions having thermal control are contemplated by the disclosure.

In some embodiments, a hair bleaching composition comprising at least two thermal control agents according to the disclosure may be mixed with a developer composition at a ratio ranging from about 1:5 to about 5:1, such as from about 1:4 to about 4:1, about 1:3 to about 3:1, or about 1:2 to about 2:1, or is, for example, about 5:1, about 4:1, about 3:1, about 2:1, about 1.5:1, about 1:1, about 1:1.5, about 1:2, about 1:3, about 1:4, or about 1:5. In other embodiments, a hair bleaching composition according to the disclosure is combined with a developer composition at a ratio of about 1:1 to about 1:2, or about 1:2 to about 1:4. In still further embodiments, a hair bleaching composition according to the disclosure may be combined with a developer composition in amounts such that the ratio of thermal control agents in the hair bleaching composition to oxidizing agent in the developer composition ranges from about 1:1 to about 1:4, about 1:1 to about 1:3, about 1:2 to about 1:3, or about 1:2.5 to about 1:3, for example is about 1:1, is about 1:2, is about 1:2.5, is about 1:2.8, or is about 1:3.

According to various embodiments, when a hair bleaching composition according to the disclosure is mixed with a developer composition to form a hair color-altering composition, the peak temperature of the hair color-altering composition is less than 70° C., for example less than about 65° C., less than about 60° C., less than about 58° C., less than about 55° C., less than about 53° C., or less than about 50° C.

According to further embodiments, the methods comprise mixing a thermal control composition with a developer composition and a hair bleaching composition not according to the disclosure, to prepare a hair color-altering composition having thermal control, e.g., a peak temperature of less than 70° C., for example less than about 65° C., less than about 60° C., less than about 58° C., less than about 55° C., less than about 53° C., or less than about 50° C. In certain embodiments, the hair bleaching composition not according to the disclosure does not comprise at least two thermal control agents in the amounts and/or ratios described herein, for example a commercially available hair bleaching composition may be used.

Methods of reducing the peak temperature of a hair-color altering composition are therefore also contemplated. In various embodiments, the methods comprise including the at least two thermal control agents described herein in a hair bleaching composition that is mixed with a developer composition in order to prepare a hair color-altering composition having thermal control, e.g., a peak temperature of less than 70° C., for example less than about 65° C., less than about 60° C., less than about 58° C., less than about 55° C., less than about 53° C., or less than about 50° C. In further embodiments, the methods comprise including preparing a hair color-altering composition having thermal control, e.g., a peak temperature of less than 70° C., for example less than about 65° C., less than about 60° C., less than about 58° C., less than about 55° C., less than about 53° C., or less than about 50° C., by mixing a developer composition, a hair bleaching composition, and a thermal control composition, wherein the hair color-altering composition comprises at least two thermal control agents.

Methods of Using Hair Color-Altering Compositions

Methods of altering the color of the hair, for example bleaching hair, are known. For example, after the hair bleaching composition and developer composition are mixed, the hair color-altering composition is applied to the hair (e.g., by brush, foam applicator, etc.), optionally the treated hair is covered, e.g., with foil, the composition allowed to remain on the hair for a processing time sufficient to achieve the desired alteration in the color of the hair, and then the composition is removed from the hair, e.g., by rinsing and/or shampooing the hair.

In order to achieve the desired alteration in the color of the hair, e.g., desired degree or level of lift of the color of the hair, the composition may remain on the hair for shorter or longer processing times, and may be at room temperature or at slightly elevated temperatures to reduce processing time (e.g., under a hood dryer). Exemplary processing (leave-in) times may range from about 5 minutes to about 75 minutes, such as about 10 minutes to about 65 minutes, about 15 minutes to about 55 minutes, about 20 minutes to about 50 minutes, about 20 minutes to about 30 minutes, about 25 minutes to about 45 minutes, or about 30 minutes to about 40 minutes. Typically, the higher degree or level of lift desired, the greater the amounts of alkalizing and oxidizing agents in the bleaching composition, and oxidizing agents in the developer composition, are required. However, as noted above, such increases in components leads to an increase in the peak temperature of the mixture, which can be harmful when using such hair color-altering compositions on the head of a person.

In contrast, however, methods according to the disclosure comprise applying the hair color-altering compositions described herein to the hair in order to alter the color of the hair by providing up to 9 levels of lift, such as at least 3 levels, at least 4 levels, at least 5 levels, at least 6 levels, at least 7 levels, or at least 8 levels, without the associated risk, since the hair color-altering compositions have a peak temperature of less than 70° C., for example less than about 65° C., less than about 60° C., less than about 58° C., less than about 55° C., less than about 53° C., or less than about 50° C.

In a first embodiment of using the hair color-altering compositions, the methods include applying a hair color-altering composition prepared by mixing a hair bleaching composition and a developer composition, and optionally a thermal control composition, to hair, where the hair color-altering composition has a peak temperature of less than about 60° C., less than about 58° C., less than about 55° C., less than about 53° C., or less than about 50° C.; optionally covering the treated hair, e.g. with foil; allowing the composition to remain on the hair for a processing time; and optionally rinsing the composition from the hair. In this exemplary and non-limiting first embodiment, the processing time is a standard processing time, e.g. from about 5 minutes to about 75 minutes, such as about 10 minutes to about 65 minutes, about 15 minutes to about 55 minutes, about 20 minutes to about 50 minutes, about 20 minutes to about 30 minutes, about 25 minutes to about 45 minutes, or about 30 minutes to about 40 minutes.

In a second embodiment of using the hair color-altering compositions, the methods include applying a hair color-altering composition prepared by mixing a hair bleaching composition and a developer composition, and optionally a thermal control composition, to hair, where the hair color-altering composition has a peak temperature of less than about 60° C., less than about 58° C., less than about 55° C., less than about 53° C., or less than about 50° C.; optionally covering the treated hair, e.g. with foil; allowing the composition to remain on the hair for a first processing time; optionally rinsing the hair color-altering composition from the hair; applying a hair color-altering composition prepared by mixing a hair bleaching composition and a developer composition, and optionally a thermal control composition, to the hair, where the hair color-altering composition has a peak temperature of less than about 60° C., less than about 58° C., less than about 55° C., less than about 53° C., or less than about 50° C.; optionally covering the treated hair, e.g. with foil; allowing the composition to remain on the hair for a second processing time; and optionally rinsing the hair color-altering composition from the hair. In this exemplary and non-limiting second embodiment, the first and/or second processing times may optionally be shorter than a standard processing time, such as, for example, from about 5 minutes to about 40 minutes, about 10 minutes to about 35 minutes, about 15 minutes to about 30 minutes, or about 20 minutes to about 25 minutes. The first and second processing times do not need to be the same, but a total processing time (first+second) ranging up to about 90 minutes, such as up to about 75 minutes, up to about 65 minutes, up to about 60 minutes, up to about 55 minutes, up to about 50 minutes, up to about 45 minutes, or up to about 40 minutes, may in some embodiments provide improved lift compared to a single processing time.

For measuring the degree of change in the color of hair (e.g., degree of lightening/lifting color or color deposit) after treating the hair, the color of the hair can be measured with a Minolta CM2600d spectrocolorimeter (specular components included, 10 degrees angle, illuminant D65) or Datacolor 600 spectrocolorimeter (specular components included, 8 degrees angle, illuminant D65) in the CIE L*a*b* system. According to this system, the greater the value of L, the lighter or less intense the color. Conversely, the lower the value of L, the darker or more intense the color.

Kits

The present disclosure also relates to kits, which in some embodiments include a hair bleaching composition according to the disclosure in a first compartment or container, and a developer composition in a second compartment or container. When the hair bleaching and developer composition are combined, a hair color-altering composition having thermal control is formed.

In further embodiments, the kit includes a hair bleaching composition not according to the disclosure in a first compartment or container, a developer composition in a second compartment or container, and a thermal control composition in a third compartment or container. When the hair bleaching composition not according to the disclosure, the developer composition, and the thermal control composition are combined, a hair color-altering composition having thermal control is formed.

In yet further embodiments, the kit includes a hair bleaching composition not according to the disclosure in a first compartment or container, and a thermal control composition in a second compartment or container. When the hair bleaching composition not according to the disclosure and the thermal control composition are combined with a developer composition not included in the kit, a hair color-altering composition having thermal control is formed.

Instructions, mixing components, brushes, gloves, measuring tools, etc., may also be included in the kits.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" or "a combination thereof" also relates to "mixtures thereof" and "combinations thereof." Throughout the disclosure, the terms "a mixture thereof" and "a combination thereof" is used, following a list of elements as shown in the following example where letters A-F represent the elements: "one or more elements selected from the group consisting of A, B, C, D, E, F, and a mixture thereof." The terms "a mixture thereof" or "a combination thereof" not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E. and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C. D, and F may be included, one or more of a salt of A, a salt of B, a salt of C, a salt of D, a salt of E, and a salt of F may be include, or a mixture of any two of A. B, C, D, E, F, a salt of A, a salt of B, a salt of C, a salt of D, a salt of E, and a salt of F may be included.

The salts which are referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The terms "hair bleaching composition," "developer composition," and "hair color-altering composition" are used throughout the disclosure. A "hair bleaching composition" is different than a "hair color-altering composition." A "hair bleaching composition" comprises one or more persulfate compounds and is combined with a "developer composition" comprising an oxidizing agent to form a "hair color-altering composition." Thus, a "hair bleaching composition" and a "developer composition" are both components of a "hair color-altering composition."

The term "thermal control" with respect to compositions and methods of the present disclosure indicates that when a hair bleaching composition according to the disclosure is mixed with an developer composition to form a hair color-altering composition, the peak temperature of the hair color-altering composition is lower than that of a hair color-altering composition not according to the disclosure, i.e. lower than 70° C., for example in various embodiments may be less than about 65° C., less than about 60° C., less than about 58° C., less than about 55° C., less than about 53° C., or less than about 50° C. A peak temperature less than about 65° C., less than about 60° C., less than about 58° C., less than about 55° C., less than about 53° C., or less than about 50° C. is typically considered to demonstrate thermal control. The peak temperature may, in some cases, be reached after a period of 35 minutes or less, such as 30 minutes or less, 25 minutes or less, or 20 minutes or less. A longer time needed to a reach peak temperature is indicative of improved thermal control.

The term "peak temperature" means the highest temperature that the hair color-altering composition reached after the hair bleaching composition and developer composition were mixed, before the temperature of the mixture began to fall.

Other than in the operating examples, or where otherwise indicated, all numbers expressing quantities of ingredients and/or reaction conditions are to be understood as being modified in all instances by the term "about," meaning within +/−5% of the indicated number.

All percentages, parts, and ratios herein are by weight, based upon the total weight of the compositions in which the component(s) is(are) present, unless otherwise indicated.

The term "treat" (and its grammatical variations) as used herein refers to the application of the compositions of the present disclosure onto the surface of hair. The term "treat" (and its grammatical variations) as used herein also refers to contacting hair with the compositions of the present disclosure.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3%, less than about 2%, less than about 1%, less than about 0.5%, less than about 0.1%, less than about 0.01%, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The following examples serve to illustrate embodiments of the present disclosure without, however, being limiting in nature. It will be apparent to those skilled in the art that various modifications and variations can be made in the delivery system, composition and methods of the invention without departing from the spirit or scope of the invention. Thus, it is intended that the present disclosure cover the modifications and variations that come within the scope of the appended claims and their equivalents.

EXAMPLES

Implementation of the present disclosure is demonstrated by way of the following non-limiting examples. In the Examples, all amounts are given by weight, relative to the total weight of the composition in which they are present.

Example 1—Hair Bleaching Compositions

The inventive and comparative pulverulent, substantially anhydrous hair bleaching compositions in Table 1 were prepared.

TABLE 1

|  | Inventive Composition | Comparative Compositions | |
| --- | --- | --- | --- |
|  | 1A | C1 | C2 |
| CARBOXYLIC ACID | 3.64 | 3.64 | 3.64 |
| AMMONIUM SULFATE | 71.50 | 6.51 |  |
| SODIUM STEARATE | 4.01 |  |  |
| TALC |  |  | 6.51 |
| POTASSIUM PERSULFATE | 41.60 | 41.60 | 41.60 |
| DISODIUM EDTA | 0.95 | 0.95 | 0.95 |
| ULTRAMARINES | 0.05 | 0.05 | 0.05 |
| MINERAL OIL | 2.00 | 2.00 | 2.00 |
| ALKALINE AGENTS | 11.00 | 11.00 | 11.00 |
| SODIUM METASILICATE | 14.00 | 14.00 | 14.00 |
| SODIUM SILICATE | 5.86 | 5.86 | 5.86 |
| AMMONIUM PERSULFATE | 11.60 | 11.60 | 11.60 |
| THICKENING AGENTS | 1.99 | 1.99 | 1.99 |
| SURFACTANTS | 0.80 | 0.80 | 0.80 |

Example 2—Developer Composition

The developer composition (40V) in Table 2 was prepared.

TABLE 2

|  | Developer Composition 2 |
| --- | --- |
| TRIDECETH-2 CARBOXAMIDE MEA | 0.1 to 3 |
| CETEARYL, ALCOHOL (and) CETEARETH-25 | 2.85 |
| HYDROGEN PEROXIDE | 11.75 |
| ADDITIONAL COMPONENTS | <1 |
| WATER | QS |

Example 3—Comparative Testing

Testing was carried out to assess the lift and thermal control of hair color-altering compositions prepared by mixing inventive hair bleaching composition 1A with developer composition 2, in comparison to the lift and thermal control of hair color-altering compositions prepared by mixing hair bleaching compositions C1-C2 not according to the disclosure with developer composition 2.

Example 3-1—Thermal Control Assessment

Thermal control was measured by conducting a bowl test in which 60 g of the pulverulent hair bleaching compositions 1A and C1-C2 and 60 g of the 40V developer composition 2 (1:1 ratio) were mixed together in a bowl to prepare hair color-altering compositions, which were allowed to rest in ambient conditions with a temperature probe in each mixture. The temperature was recorded every minute, and from the resulting data the peak temperature and the time needed to reach the peak temperature were determined, as shown in Table 3-1.

TABLE 3-1

Hair Color-Altering Compositions: Peak Temperature/Time

| Hair Bleaching Composition | Developer Composition | Mix Ratio | Hair Color-Altering Composition | Peak Temperature/Time to Reach |
|---|---|---|---|---|
| 1A | 2 | 1:1 | 1A/2A | 47.7° C./23 minutes |
| C1 | 2 | 1:1 | C1/2A | 40.3° C./27 minutes |
| C2 | 2 | 1:1 | C2/2A | 64.4° C./32 minutes |

As seen in Table 3-1, compositions 1A/2A and C1/2A have a peak temperature less than about 48° C., and are thus considered to demonstrate significantly better thermal control than composition C2/2A, which had a peak temperature above 64° C.

Example 3-2—Lift Assessment

Lift was evaluated by first mixing hair bleaching compositions 1A and C1-C2 with developer composition 2 at a ratio of 1:1.5 (hair bleaching composition:developer composition), applying each of the compositions to a separate swatch of hair (Level 3, Natural) at a composition:hair ratio of about 10:1, and covering the swatch in foil. The swatches were processed for about 25 minutes at about 33° C. The foil was removed, a second application of hair color-altering composition was applied, the foil replaced, and the swatches were processed a second time for about 25 minutes at about 33° C., then rinsed with water and air dried.

The change in tone of the swatches was evaluated once dry, with the tone of the swatch treated with C2/2B used as the baseline against which the lift imparted by 1A/2B and C1/2B were measured. From the data, the resultant L* values were computed and compared, as shown in Table 3-2. In particular, the lightening performance (lightness L) was measured using a Datacolor 600 spectrocolorimeter (illuminant D65, angle 8°, specular components included) in the CIE L*a*b* system. L* represents the lightness: the higher the value of L*, the more the lock is lightened. A difference in L* values (Δ L*) greater than 1.5 indicates a significant difference, since this amount is indicative of the ability of the human eye to perceive differences, with a higher Δ L* equating to better lift.

TABLE 3-2

Hair Color-Altering Compositions: Lift

| Hair Bleaching Composition | Developer Composition | Mix Ratio | Hair Color-Altering Composition | Δ L* |
|---|---|---|---|---|
| 1A | 2 | 1:1.5 | 1A/2B | 0.93 |
| C1 | 2 | 1:1.5 | C1/2B | −3.39 |
| C2 | 2 | 1:1.5 | C2/2B | — |

As seen in Table 3-2, composition 1A/2B imparted significant improvement in lift over comparative compositions C1/2B (with C2/2B as the baseline).

This Example therefore demonstrates a synergistic result in terms of lift and thermal control using hair color-altering compositions prepared by mixing a hair bleaching composition according to the disclosure with a developer composition. The data in Tables 3-1 and 3-2 demonstrate that a hair color-altering composition having a reduced peak temperature, and which is able to provide superior lift to the color of the hair, can be achieved.

The invention claimed is:

1. A pulverulent hair bleaching composition comprising:
   (a) at least two thermal control agents comprising sodium stearate and ammonium sulfate;
   (b) at least one persulfate compound; and
   (c) at least one silicate compound chosen from sodium silicate, sodium metasilicate, or mixtures thereof;
   wherein sodium stearate is present in an amount greater than about 2.5% by weight, relative to the total weight of the pulverulent hair bleaching composition;
   wherein ammonium sulfate is present in an amount greater than about 2% by weight, relative to the total weight of the pulverulent hair bleaching composition;
   wherein the weight ratio of sodium stearate to ammonium sulfate is greater than about 1:1; and
   wherein the composition comprises less than 1% water by weight, relative to the total weight of the pulverulent hair bleaching composition.

2. The pulverulent hair bleaching composition of claim 1, wherein the total amount of the thermal control agents ranges from about 4% to about 20% by weight, relative to the total weight of the pulverulent hair bleaching composition.

3. The pulverulent hair bleaching composition of claim 1, wherein the at least one silicate comprises sodium metasilicate, present in amount of at least 5% by weight, relative to the total weight of the pulverulent hair bleaching composition.

4. The pulverulent hair bleaching composition of claim 1, wherein the at least one persulfate compound is chosen from potassium persulfate, ammonium persulfate, sodium persulfate, or mixtures thereof.

5. The pulverulent hair bleaching composition of claim 1, wherein the at least one persulfate compound comprises ammonium persulfate, present in an amount of at least about 5% by weight, relative to the total weight of the pulverulent hair bleaching composition.

6. An aqueous hair color-altering composition comprising:
   1) a pulverulent hair bleaching composition comprising:
      (a) at least two thermal control agents comprising sodium stearate and ammonium sulfate;
      (b) at least one persulfate compound comprising ammonium persulfate; and
      (c) at least one silicate compound chosen from sodium silicate, sodium metasilicate, or mixtures thereof;
      wherein the weight ratio of sodium stearate to ammonium sulfate is greater than about 1:1; and
   2) a developer composition comprising at least one oxidizing agent;
   wherein the pulverulent hair bleaching composition and the developer composition are mixed to form the aqueous hair color-altering composition.

7. The aqueous hair color-altering composition of claim 6, wherein the total amount of the thermal control agents ranges from about 4% to about 20% by weight, relative to the total weight of the pulverulent hair bleaching composition.

8. The aqueous hair color-altering composition of claim 6, which has a peak temperature of less than about 60° C.

9. The aqueous hair color-altering composition of claim 6, wherein the pulverulent hair bleaching composition and the developer composition are mixed at a ratio ranging from about 1:3 to about 3:1.

10. The aqueous hair color-altering composition of claim 6, wherein the at least one silicate comprises sodium metasilicate, present in amount of at least about 5% by weight, relative to the total weight of the pulverulent hair bleaching composition.

11. The aqueous hair color-altering composition of claim 6, wherein the at least one persulfate compound comprises at least one additional persulfate chosen from potassium persulfate, sodium persulfate, and mixtures thereof.

12. The aqueous hair color-altering composition of claim 6, wherein the ammonium persulfate is present in an amount of at least about 5% by weight, relative to the total weight of the pulverulent hair bleaching composition.

13. A method for preparing an aqueous hair color-altering composition comprising mixing a pulverulent hair bleaching composition and a developer composition to form a mixture having a peak temperature less than about 60° C.,
wherein the pulverulent hair bleaching composition comprises:
(a) at least two thermal control agents comprising sodium stearate and ammonium sulfate;
(b) at least one persulfate compound; and
(c) at least one silicate compound chosen from sodium silicate, sodium metasilicate, or mixtures thereof;
wherein sodium stearate is present in an amount greater than about 2% by weight, relative to the total weight of the pulverulent hair bleaching composition;
wherein ammonium sulfate is present in an amount greater than about 1.5% by weight, relative to the total weight of the pulverulent hair bleaching composition;
wherein the weight ratio of sodium stearate to ammonium sulfate is greater than about 1:1;
wherein the developer composition comprises at least one oxidizing agent; and
wherein the mixture comprises water.

14. The method of claim 13, wherein the total amount of the thermal control agents ranges from about 4% to about 20% by weight, relative to the total weight of the pulverulent hair bleaching composition.

15. The method of claim 13, wherein the peak temperature of the mixture is less than about 58° C.

16. The method of claim 13, wherein the at least one oxidizing agent comprises hydrogen peroxide.

17. The method of claim 13, wherein the at least one silicate comprises sodium metasilicate, present in amount of at least about 5% by weight, relative to the total weight of the pulverulent hair bleaching composition.

18. The method of claim 13, wherein the at least one persulfate compound is chosen from potassium persulfate, ammonium persulfate, sodium persulfate, and mixtures thereof.

19. The method of claim 13, wherein the at least one persulfate compound comprises ammonium persulfate, present in an amount of at least about 5% by weight, relative to the total weight of the pulverulent hair bleaching composition.

20. A kit comprising:
1) a first compartment comprising a pulverulent hair bleaching composition comprising:
(a) at least two thermal control agents comprising sodium stearate and ammonium sulfate;
(b) at least one persulfate compound; and
(c) at least one silicate compound chosen from sodium silicate, sodium metasilicate, or mixtures thereof;
wherein sodium stearate is present in an amount greater than about 2.5% by weight, relative to the total weight of the pulverulent hair bleaching composition;
wherein ammonium sulfate is present in an amount greater than about 2% by weight, relative to the total weight of the pulverulent hair bleaching composition; and
wherein the weight ratio of sodium stearate to ammonium sulfate is greater than about 1:1; and
2) a second compartment comprising a developer composition comprising at least one oxidizing agent; and
3) optionally, a third compartment comprising a conditioning composition.

21. A hair-color altering composition comprising:
(a) at least two thermal control agents comprising sodium stearate and ammonium sulfate;
(b) at least one persulfate compound;
(c) at least one silicate compound;
(d) at least one oxidizing agent; and
(e) water;
wherein the ratio of sodium stearate to ammonium sulfate is greater than about 1:1; and
wherein the peak temperature of the hair color-altering composition is less than about 60° C.

* * * * *